(12) United States Patent
Wang et al.

(10) Patent No.: US 8,759,032 B2
(45) Date of Patent: Jun. 24, 2014

(54) GENETICALLY ENGINEERED STRAIN WSJ-IA FOR PRODUCING ISOVALERYL SPIRAMYCIN I

(75) Inventors: Yiguang Wang, Beijing (CN); Yang Jiang, Shen Yang (CN); Shengwu Yang, Shen Yang (CN); Xiaofeng Zhao, Shen Yang (CN)

(73) Assignee: Shen Yang Tonglian Group Co., Ltd., Shen Yang (CN)

( * ) Notice: Subject to any disclaimer, the term of this patent is extended or adjusted under 35 U.S.C. 154(b) by 0 days.

(21) Appl. No.: 13/811,340

(22) PCT Filed: Jul. 21, 2011

(86) PCT No.: PCT/CN2011/001194
§ 371 (c)(1),
(2), (4) Date: Jan. 21, 2013

(87) PCT Pub. No.: WO2012/009963
PCT Pub. Date: Jan. 26, 2012

(65) Prior Publication Data
US 2013/0130324 A1 May 23, 2013

(30) Foreign Application Priority Data
Jul. 23, 2010 (CN) .......................... 2010 1 0237595

(51) Int. Cl.
| C12P 19/62 | (2006.01) |
| C12P 19/60 | (2006.01) |
| C12P 19/44 | (2006.01) |
| C12N 1/21 | (2006.01) |
| C12R 1/465 | (2006.01) |
| C12N 1/20 | (2006.01) |
| C12N 15/70 | (2006.01) |
| C12N 15/76 | (2006.01) |
| C12N 9/10 | (2006.01) |

(52) U.S. Cl.
CPC ................. C12P 19/62 (2013.01); C12R 1/465 (2013.01); C12N 1/20 (2013.01)
USPC .. 435/76; 435/252.1; 435/252.3; 435/252.35; 435/75; 435/74; 435/72

(58) Field of Classification Search
None
See application file for complete search history.

(56) References Cited

FOREIGN PATENT DOCUMENTS

| CN | 1405299 | 3/2003 |
| CN | 101054553 | 10/2007 |
| CN | 101649325 | 2/2010 |
| CN | 101914481 | 12/2010 |
| CN | 101914482 | 12/2010 |
| JP | 53-34788 | 3/1978 |

OTHER PUBLICATIONS

Arisawa et al., Cloning and nucleotide Sequences of two genes involved in the 4"-O-acylation of macrolide antibiotics from Streptomyces thermotolarences, Biosci. Biotech. Biochem., 1993, 57, 2020-25.*
Guangdong et al., Construction and physiological studies on stable bioengineered strain of shengjimycin, J. Antibiotics, 2001, 54, 66-73.*
Ma et al., Construction of 4'-isovalerylspiramycin-I-producing strain by in-frame partial deletion of 3-O-acyltransferase gene in Streptomyces spiramycetius WSJ-1, the bitespiramycin producer, Curr. Microbiol., 2011, 62, 16-20.*
CGMCC No. 4.1501, China General Microbiological Culture Collection Center, 2013, www.cgmcc.net/index.php/Contents/show/id/12851.*
Cox et al., Restriction of bacteriophage plaque formation in Streptomyces spp., J. Bacteriology, 1984, 159, 499-504.*
International Search Report of PCT/CN2011/001194 dated Oct. 27, 2011 (in Chinese and English).
Wei, et al. "Fermentation Scale-up Experiment of Genetically Engineered Strain of Isovaleryl-Spiramycin", Chinese Journal of Antibiotics, ISSN: 1001-8689, vol. 21, No. 3, Jun. 30, 1996, 4 pages.
Sun, et al. "Isolation and Structure Determination of Shengjimycin E (4"-isovalerylspiramycin I)", Chinese Journal of Antibiotics, ISSN: 1001-8689, vol. 25, No. 1, Feb. 29, 2000, 5 pages.
Li, et al. "Leucine Improves the Component of Isovalerylspiramycins for the Production of Bitespiramycin", Bioprocess and Biosystems Engineering, ISSN: 1615-7591, vol. 32, No. 5, Aug. 31, 2009, 7 pages.
Wang, et al. "A Combined Strategy to Simultaneously Improve the Component of Isovalerylspiramycin in a Bitespiramycin (4"-O-acylspiramycins) Complex and its Biological Titre", Process Biochemistry, ISSN: 1359-5113, vol. 43, No. 9, Sep. 30, 2008, 5 pages.
English Abstract of CN 101914482 from Espacenet, 2 pages, 2010.
English Abstract of CN 101914481 from Espacenet, 1 page, 2010.
English Abstract of CN 101054553 from Espacenet, 1 page, 2007.
English Abstract of CN 101649325 from Espacenet, 2 pages, 2010.
English Abstract of CN 1405299 from Espacenet, 1 page, 2003.
English Abstract of JP 53-34788 from Espacenet, 1 page, 1978.
International Search Report of PCT/CN2011/001194 dated Oct. 27, 2011 (in Chinese and English), 8 pages.

* cited by examiner

*Primary Examiner* — Rebecca Prouty
*Assistant Examiner* — Todd M Epstein
(74) *Attorney, Agent, or Firm* — Rankin, Hill & Clark LLP

(57) ABSTRACT

A genetically engineered strain WSJ-IA for producing isovaleryl spiramycin I. Also provided is a method for preparing the strain, including the steps of: (a) constructing a recombinant plasmid including a double gene ist-acyB2; (b) transforming the plasmid into an isovaleryl spiramycin I-producing strain to obtain the strain WSJ-IA. The level of isovaleryl spiramycin I produced by fermentation of the strain WSJ-IA is increased 1.7 times and the fermentation potency thereof increased 4.14 times in comparison with the strain exclusively including a single gene ist.

2 Claims, 3 Drawing Sheets

GENETICALLY ENGINEERED STRAIN WSJ-IA FOR PRODUCING ISOVALERYL SPIRAMYC expression of ist gene. The model *streptomyces* strain: Variable Lead Green *Streptomyces* containing complete ist—as well as acyB2-regulatory genes was able to convert 67-79% of the externally added tylosin to 4"-isovaleryl tylosin, whereas the same strain of *Streptomyces* containing only ist gene, or ist gene with incomplete acyB2 gene, converted only 0-2.4% of the added tylosin [Arisawa A et al: Biosci Biotechnol Biochem 1993, 57(12): 2020-2025]. By transferring recombinant plasmid of autonomous replication form (vectors pIJ702 or pIJ943) containing ist- and acyB2 genes into tylosin producing bacterium (*Streptomyces fradiae*), under the condition of external addition of a drug (thiopeptin), the transformant mainly produced tylosin in fermentation, besides a minor amount of 4"-isovaleryltylosin (ca. 56 g/mL) [Arisawa A. et al: J Antibiotics 1996,49(4):349-354] could be detected. However, no reports on the increase of 4"-isovaleryltylosin yield or higher content of single component in the mixture by transferring ist- and acyB genes into tylosin producing bacterium have been published up to now.

acyB2 regulatory gene and the transcriptional regulatory protein Srm28c in the spiramycin producing bacterium (*Streptomyces ambofaciens*) are homologous [Fatma Karray et al Microbiology 2007,153,4111-4122], their degree of identity is 69%, the degree of identity of acyB2 and regulatory protein tylR in tylosin producing bacterium (*Streptomyces fradiae*) is 41%, tylR is the positive regulatory protein of the biosynthesis in tylosin producing bacterium, it regulates the expression of a polyketide synthase module (tylGI) in tylosin producing bacterium, and plays a regulatory role on the tylosin glycosyl synthesis as well as the polyketone ring oxidation. High expression of tylR gene in the tylosin producing bacterium can increase the yield of tylosin [George S. et al., Mol. Microbiology 2004,54(5):1326-1334]. However, the method of integration of ist gene into the spiramycin producing bacterium, which is homologous as the acyB2, by means of chromosome-recombinant plasmid homologous DNA recombination technology, only resulted in the production of mixture of isovaleryl spiramycin, with a yield of as high as 800 mg/mL [Shang Guangdong et al. Chinese Journal of Biotechnology, 1999,15(2):171]. This demonstrated that only by transferring ist gene into a strain containing regulatory gene similar with acyB2 would not be able to increase significantly the yield and component content of the target product.

This laboratory demonstrated that by concatenating ist gene using genetic engineering technique, to increase the copy number of ist gene in spiramycin producing bacterium to increase ist gene dosage, the capability of the bacteria to isovalerylate was also increased; it was also demonstrated that by substituting the original ist gene promoter sequence with a promoter with strong activity, such as erythromycin resistance gene ermE promoter sequence, the expression of ist gene could be increased. This increases the production of isovaleryl spiramycin by 62% with the gene engineered bacterium [Patent application No. 200910148767.8].

The aim of this invention is to obtain bacterial strains yielding high content of Bitespiramycin single component—isovaleryl spiramycin I, as well as high productivity by means of expression of ist gene linked with regulatory gene acyB2 in a strain, which has already been obtained, capable of producing only the component of isovaleryl spiramycin I, using a highly efficient and stable expression system. To attain this aim, it is necessary to overcome the obstacles of the restriction of the antibiotic producing bacteria of practical value on the gene modification by exogenous gene, thereby improving the conversion rate of the exogenous DNA. Meanwhile, it is necessary to select vector systems for stable express, such that the genetically engineered bacteria can be suitable for large-scale industrial production. This invention proposes to adopt an integrated vector for non-autonomous replication in *Streptomyces*, such a vector contains the *Streptomyces* phage integrase enzyme as well as the attachment sites, and contains only the *E. coli* replicon, to facilitate the preparation in *E. coli*; meanwhile the vector lacks *Streptomyces* replicon. When it enters *Streptomyces* cells, the integration relies on the attachment sites (attP) on the carrier and specific attachment sites of the host bacteria. Therefore, the exogenous gene may be stably expressed in large scale production. The researches on the co-expression of said isovaleryl acylase gene ist and the regulatory gene acyB2 in isovaleryl spiramycin I producing bacterium to increase the yield and content of isovaleryl spiramycin I, as well as the studies on pilot-scale experimental production, have not been found reported to date at home and abroad.

Contents of the Invention

1, This invention provides a strain of genetically engineered bacterium producing high yield and high content of isovaleryl spiramycin I component, said engineered bacterium is a clone strain with isovaleryl transferase gene ist linked with acyB2 regulatory gene co-expressed in isovaleryl spiramycin I producing bacterium WSJ-2.

2, This invention provides the construction of the strain of gene engineered bacterium producing high yield and high content of isovaleryl spiramycin I component, said construction is to use the total DNA of heat-resistant *Streptomyces* (*Streptomyces thermotolarences* CGMCC4.1501) as template, design the primers according to the ist-acyB2 sequences announced by NCBI, and to obtain the linked ist-acyB2 gene fragment by means of PCR, insert appropriate cleavage sites; it is also proposed to ligate ist and acyB2 gene fragments, respectively, with the integrative vector transferrable to the isovaleryl spiramycin I producing bacteriuml strain in appropriate cleavage sites, to construct ist-acyB2 gene recombinant plasmid. The ist-acyB2 gene recombinant plasmid is subsequently inserted into isovaleryl spiramycin I producing bacterium WSJ-2, after which PCR is carried out to verify that ist-acyB2 is integrated in the transformant genome to obtain WSJ-IA.

3, This invention proposes to identify the characteristics of the *Streptomyces* strain WSJ-IA in accordance with the standards of the classification and identification of *Streptomyces*.

4, Using the isovaleryl spiramycin I producing bacterium WSJ-2 that contains ist monogene as control, this invention tested the fermentation performance of the WSJ-IA strain, including measurement of the fermentation titer of the WSJ-IA strain using microbiological method, and the isovaleryl spiramycin I content in the fermentation broth by means of HPLC quantitative analysis. The results showed that introduction of acyB2 regulatory gene can significantly improve the content as well as the yield of isovaleryl spiramycin I component by the strain.

Effect of this invention: The positive effect of invention is to show that introduction of acyB2 regulatory gene into the isovaleryl spiramycin I producing bacteriuml strain WSJ-2 can increase the fermentation titer by 414%, and increase the content of isovaleryl spiramycin component I by 170.2%. The high isovaleryl spiramycin I producing strain constructed in this invention has been pilot tested in a 2 ton fermentation tank, the accumulated isovaleryl spiramycin I samples have been used for pharmacodynamic studies. The application of this strain into the industrial production of this antibiotic component can not only simplify the quality control and testing standard of the product, but also offer conditions for the preparation of the injectable formulation of isovaleryl spiramycin.

THE DESCRIPTIONS OF THE DRAWINGS

Figure 3:
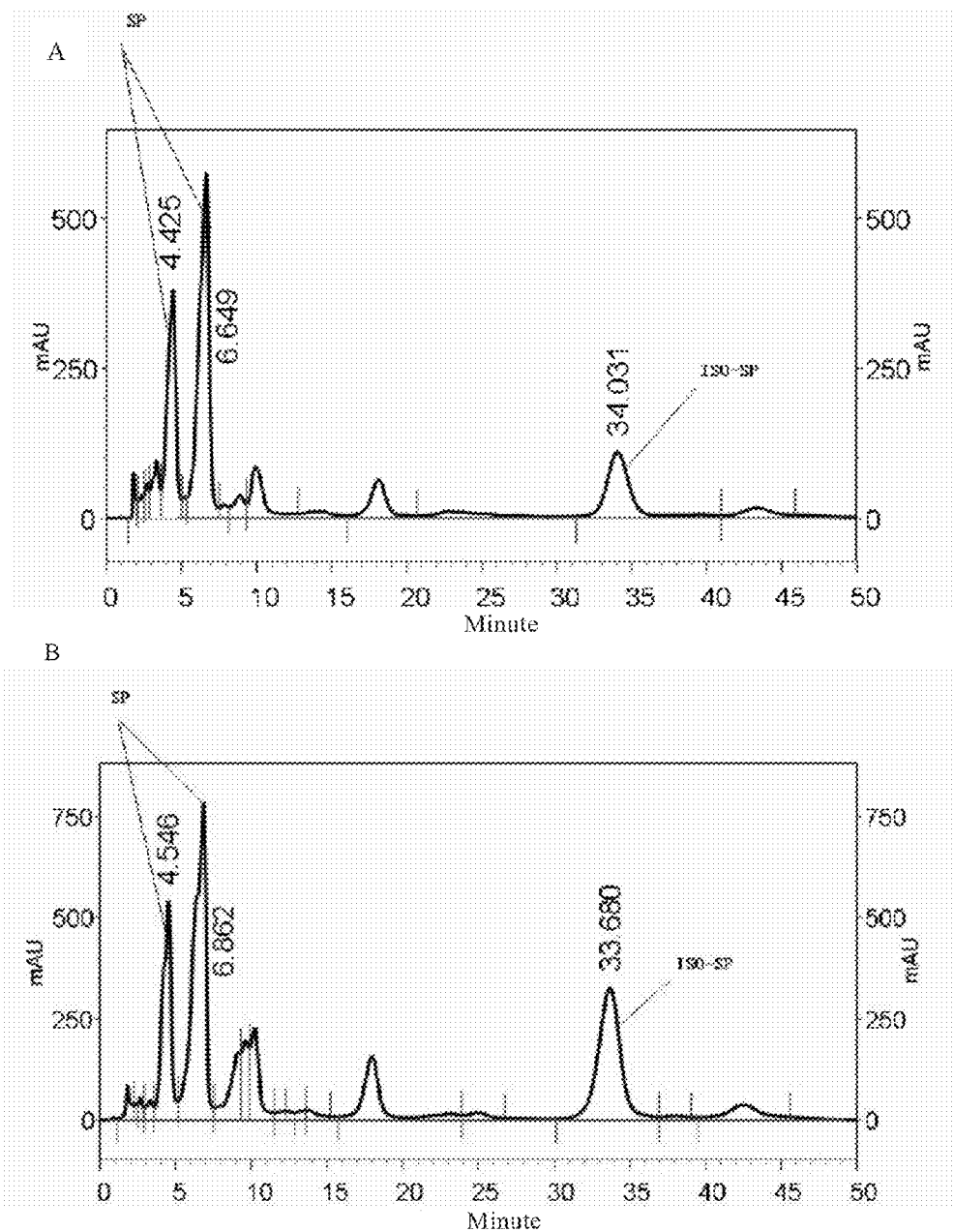

FIG. 3 is the HPLC result of isovaleryl spiramycin component I in the fermentation product by bacterial strain WSJ-IA containing ist-acyB2 gene recombinant plasmid pSET52-ia; wherein A: WSJ-2 control bacterium; B: WSJ-IA, gene engineered bacterium containing ist gene and regulatory gene acyB2; SP-spiramycin; ISO-SP-isovaleryl spiramycin I.

EMBODIMENTS OF THE INVENTION

Following examples only serve to help the technicians of this field to better understand this invention, which are by no means any restriction to this invention.

Example 1

Construction of Recombinant Plasmid pSET52-ia Containing Dual Gene Ist-acyB2

Figure 1:
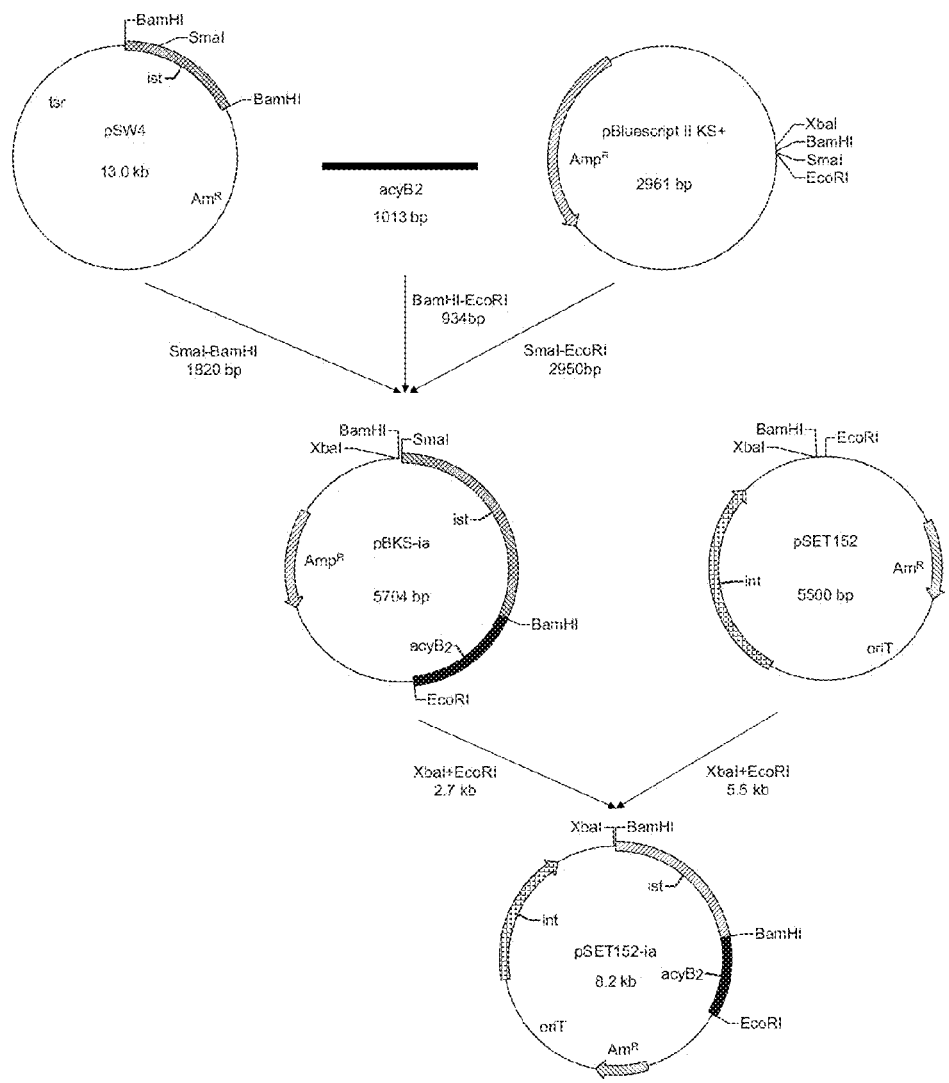
FIG. 1 is the construction of ist-acyB2 gene recombinant plasmid pSET52-ia.

The recombinant plasmid pSW4 constructed previously in this laboratory [Shang Guangdong et al., Chinese Journal of Biotechnology, 1999, 15(2):171] was digested with SmaI-BamHI enzyme to obtain complete ist gene and 1820 segment containing upstream part of acyB2 gene, using total DNA of heat-resistant *Streptomyces* provided by China General Microbiological Culture Collection Center (*Streptomyces thermotolarences* CGMCC4.1501) as a template, to design primers according to acyB2 sequence announced by NCBI.

p1: CGCTCAGGGACGCAAGACC (SEQ ID NO:7) and P2: CCGGAATTCGCCCCGTGACCTCACCGTC (SEQ ID NO:8), PCR temperature: 94° C. predenaturation for 2 min; 94° C. for 30 s, 60° C. for 30 s, 72° C. for 1 min, 28 cycles; extending at 72° C. for 5 min, to obtain 1013 bp segment of the downstream part of acyB2 gene. BamHI-EcoRI enzyme was used to digest the PCR product to obtain 934 bp segment, the aforementioned segments digested by SmaI-BamHI (1820 bp) and BamHI-EcoRI (934 bp) were ligated into in pBluesript II KS(+) vector (E•Merck) by the restriction enzyme sites SmaI-EcoRI, to obtain gene recombinant plasmid pBKS-ia containing ist and complete acyB2. pSET152 plasmid, were ligated into the integrated *E. coli*/Streptomyces conjugative transfer plasmid via the restriction sites by XbaI-EcoRI enzyme [Bierman M. et al Gene 1992,116,43-49, from shared gene bank, www.genecool.com], to obtain ist-acyB2 gene recombinant plasmid pSET52-ia (The experimental method was according to operation procedures, TAKARA Biotechnology (Dalian) Co., Ltd.). Construction process is shown in FIG. 1.

Example 2

Recombinant Plasmid pSET52-ia Convertion of Isovaleryl Spiramycin I Producing Bacterium WSJ-2

Isovaleryl spiramycin I producing bacterium WSJ-2 was constructed by this laboratory [Chunyan Ma et al. Current Microbiology, 2011, 62:16-20]. Said strain was cultured on slant medium [Soybean cake flour 2.0%, glucose 1.0%, starch 3.0%, $CaCO_3$, 0.5%, NaCl, 0.4%, agar 2.0%] at 28° C. for 7-10 days, to prepare protoplast according to the procedures described in the literature [D. A. Hopwood et al. Genetic manipulation of *Streptomyces*, A Laboratory Manual, Norwich; John Innes Foundation UK, 1985], Specifically, a piece of strain culture was scooped to inoculate onto R2YE medium containing sucrose, cultured at 28° C. for 2-4 days, the same medium was inoculated by transferring 10% of the above culture with addition of 0.5% glycine, cultured for 20 hours. The mycelium was collected by centrifugation, washed 2-3 times with 10.3% sucrose solution, the mycelium was bacteriolyzed at 37° C. in the P solution containing 2 mg/ml lysozyme for 15-60 min, filter through cotton to obtain protoplasts. To overcome the restriction of the isovaleryl spiramycin I producing bacterium WSJ-2 to exogenous gene modification, first, recombinant plasmids pSET52-ia was transferred to methylation-deficient *E. coli* 12567 [Mac Neil et al Gene 1992, 111, 61-68, from shared gene bank, www.genecool.com]. Plasmid DNA from the transformant was extracted, subsequently transferred into protoplast under the mediation of PEG, coated on R2YE solid medium. After culture for at 28° C. 24 hours, the culture was covered with solution containing apramycin to attain a final apramycin concentration of 50 μg/ml in the medium, and cultured for 7-10 days, to pick the resistant transformants. The transformants are subcultured continuously without dosing, and then test after dosing to obtain the isovaleryl spiramycin I producing bacterium WSJ-IA with stable expression of resistant recombinant plasmid pSET52-ia.

Figure 2:
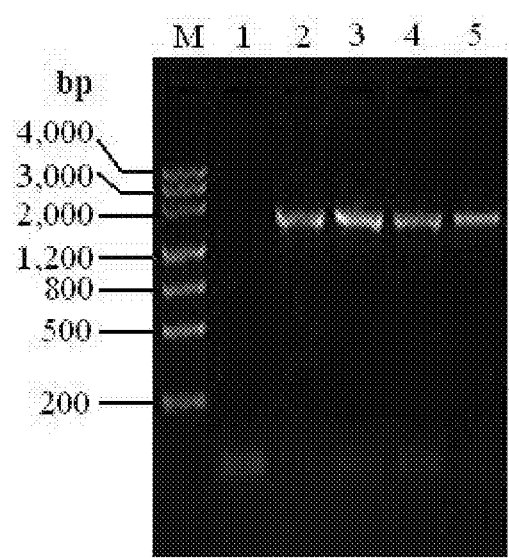
FIG. 2 is the PCR result of chromosome of the bacterial strain producing isovaleryl spiramycin and containing ist-acyB2 gene; wherein M: DNA MarkerIII; 1-WSJ-2 control bacterium; 2-5: Transformants WSJ-IA 1-4.

The primers for upstream of ist gene and downstream of acyB2 gene P3: GAGGTAGAAGGCGAAGGT (SEQ ID NO:9) and P4: CGTCAGATGCCAGTTCAC (SEQ ID NO:10) was designed, PCR was carried out for the total DNA of control bacterium WSJ-2 and transformant (4) of WSJ-IA put forward in the present invention as templates, PCR procedure were: 94° C. predenaturation for 2 min; 94° C. for 30 s, 60° C. for 30 s, 72° C. for 2 min, 28 cycles; 72° C. extension for 5 min (FIG. 2). The obtained results showed that 1733 bp PCR product could be obtained from WSJ-IA genome, whereas no PCR product was obtained from the control strain, this meant that ist-acyB2 gene had been integrated into the genome of the target strain successfully. Said strain has been sent to China General Microbiological Culture Collection Center, No. 1, 3rd Bldg., Beichen West Road, Chaoyang District, Beijing, on Jun. 25, 2010, to be preserved. Accession number: No.CGMCC 3942, category name: *Streptomyces spiramyceticus*.

Example 3

Identification and Confirmation of the Characteristics of the Strain WSJ-IA In reference to "classification and identification of actinomycetes" [Yan Xunchu ed., 1992], this invention identified and confirmed the characteristics of the WSJ-IA strain.

1. WSJ-IA Culture Morphology and Physiological and Biochemical Characteristics (1) Culture Characteristics Aerial mycelium, substrate mycelium and the color of the soluble pigment of the strain cultured in different medium were observed, the results are shown in Table 1.

(2) Microscopic Characteristics

Fibrillae of spores were soft and winding, hook-like and spiral; spores cylindrical and oval.

TABLE 1

Culture morphology of WSJ-IA strain

| Culture characteristics | Aerial mycelium | Substrate mycelium | Soluble pigment |
|---|---|---|---|
| Czapek medium | extremely few, white | lotus seed white | not observed |
| Glucose asparagine medium | extremely few, off-white | yellow-brown | not observed |
| Glycerol asparagine medium | no aerial mycelium | lotus seed yellow | not observed |
| Inorganic salt starch medium | no aerial mycelium | light khaki | not observed |
| ISP-2 medium | white | earthy brown | not observed |
| Oat flour medium | white | Ivory yellow | not observed |
| Gause's No. 1 medium | extremely few, ivory-white | light khaki | not observed |
| Santa's medium | no aerial mycelium | Chestnut Brown | not observed |

Note:
Czapek medium: Cane sugar: 30 g, $NaNO_3$ 3.0 g, $MgSO_4 \cdot 7H_2O$ 0.5 g, KCl 0.5 g, $FeSO_4 \cdot 4H_2O$, $K_2HPO_4$ 1.0 g, agar 15.0 g, distilled water 1.0 L, pH 6.0-6.5.
Glucose asparagine medium: Glucose 10 g, asparagine 0.5 g, $K_2HPO_4$ 0.5 g, agar 15.0 g, distilled water 1.0 L, pH 7.2-7.4.
Glycerol asparagine medium: Glycerol 10 g, asparagine 0.5 g, $K_2HPO_4$ 0.5 g, agar 15.0 g, distilled water 1.0 L, pH 7.2-7.4.
Inorganic salt starch medium: Soluble starch 10.0 g, $MgSO_4 \cdot 7H_2O$ 1.0 g, NaCl 1.0 g, $(NH_4)_2SO_4$ 2.0 g, $CaCO_3$ 2.0 g, $K_2HPO_4$ 1.0 g, $MnCl_2 \cdot 4H_2O$ 10 mg, $FeSO_4$ 10 mg, $ZnSO_4 \cdot 7H_2O$ 10 mg, agar 15.0 g, distilled water 1.0 L, pH 7.2.
ISP-2 medium: Yeast extract 4.0 g, Malt extract 10.0 g, glucose 4.0 g, agar 20.0 g, distilled water 1.0 L, pH 7.2-7.4.
Oat flour medium: Oat flour 20.0 g, Trace salt solution 1 mL, agar 15 g, distilled water 1.0 L, pH 7.2, wherein: Trace salt solution: $FeSO_4 \cdot 7H_2O$ 0.1 g, $MnCl_2 \cdot 4H_2O$ 0.1 g, $ZnSO_4 \cdot 7H_2O$ 0.1 g, 100 mL distilled water.
Gause's No. 1 medium: Soluble starch 20.0 g, $KNO_3$ 1.0 g, $K_2HPO_4$ 0.5 g, $MgSO_4 \cdot 7H_2O$ 0.5 g, NaCl 0.5 g, $FeSO_4 \cdot 7H_2O$ 0.01 g agar 15.0 g, distilled water 1.0 L, pH 7.2-7.4.
Santa's medium: $KH_2PO_4$ 0.5 g, $MgSO_4 \cdot 7H_2O$ 0.5 g, citric acid 2.0 g, Ferric ammonium citrate 0.05 g, glycerol 60 mL, Asparagine 4.0 g, agar 15.0 g, distilled water 1.0 L, pH 7.4.

(3) Physiological and Biochemical Characteristics

A. Detection the utilization of a carbon source by the WSJ-IA strain in the basal media selected.

Basal medium: $(NH_4)_2SO_4$ 2.0 g, $MgSO_4 \cdot 7H_2O$ 0.2 g, $NaH_2PO_4 \cdot H_2O$ 0.5 g, $CaCl_2 \cdot 2H_2O$ 0.1 g, $K_2HPO_4$ 0.5 g, distilled water 1.0 L. Add 0.1%-0.5% of the carbon source to be measured into the basal medium. After sterilization, inoculate the medium with bacterial suspension, culture at 28° C., transplant for three generations successively. Determine utilization of the WSJ-IA strain on the carbon source according to the status of cell growth.

B. Basal medium measurement of malonic acid utilization: Basal medium: Yeast extract 1.0 g, $(NH_4)_2SO_4$ 2.0 g, $K_2HPO_4$ 0.6 g, $KH_2PO_4$ 0.4 g NaCl 2.0 g, sodium malonate 3.0 g, bromothymol blue 0.025 g, distilled water 1.0 L, pH 7.0-7.4. After sterilization, inoculate the medium with bacterial suspension, culture at 28° C. for 1-2 days, malonic acid utilization by the bacteria is indicated when the medium turns its color from green to blue.

C. Basal medium measurement of tartaric acid utilization: Basal medium: peptone 10.0 g, NaCl 5.0 g, sodium tartrate 10.0 g, bromothymol blue (0.2%) 12.5 mL, distilled water 1.0 L, sterilize the medium before use. Prepare the saturated solution of lead acetate simultaneously. Inoculate the medium with bacterial suspension, culture at 28° C. for 14 days. Add isometric lead acetate solution, utilization of tartaric acid by the bacteria is indicated when the color of the medium turns green yellow with small amount of lead acetate precipitation.

D. liquefaction of gelatin: Basal medium: peptone 5.0 g, gelatin 100-150 g, distilled water 1.0 L, pH 7.2-7.4, and sterilized. After culture of the bacteria for 18-24 hours, puncture inoculate the suspension into gelatin medium, at the same time set the non-inoculated control. Culture the samples at 20° C. in an incubator for 2, 7, 10, 14 and 30 days, observe the cell growth and gelatin liquefaction at room temperature low than 20° C. If the results show the growth of bacteria, and that no depression of the gelatin surface is observed and the gelatin clot is stable, these means gelatin liquefaction negative.

E. Milk reaction: Boil fresh milk and place it in the refrigerator overnight. Take underlying skimmed milk, add 4 ml of a 2.5% litmus aqueous solution (2.5 g litmus immersed in 100 ml distilled water overnight, filtered subsequently), into 100 ml skimmed milk, add the mixture into test tubes to heights of about 4 cm, respectively. Sterilize the test tubes and inoculate with the strain, culture at 28° C. for 1, 3, 5, 7, 14 and 30 days. The results show that milk peptonized into cakes.

F, Reductin of nitrates: Nutrient agar medium 1.0 liters, $KNO_3$ 1.0 g, pH 7.0-7.6, Dispense 4-5 mL above medium into each of the test tubes, then sterilize. Griess reagents: a) dissolve 0.5 g sulfanilic acid in 150 ml dilute acetic acid (10%); b) dissolve 0.1 g-naphthyl amine in 20 ml distilled water and 150 ml dilute acetic acid (10%). Diphenylamine reagent: dissolve 0.5 g diphenylamine in 100 ml concentrated sulfuric acid, dilute with 20 ml distilled water. Inoculate the strain into nitrate medium, culture at 28° C. for 1, 3, 5 days, add small amount of the 1-, 3-, 5-day culture in clean tubes, add in a drop of a) and b) reagents, respectively, the color of the solution turns red demonstrated the reduction of nitrate to nitrite; add in a drop of diphenylamine reagent, no blue reaction can be observed.

G. Tyrosinase test: Inoculate the strain in Gause's No. 1 liquid medium at 28° C. for 7, 9, 12 days, respectively, sample 2 ml culture broth, centrifuged and fetch the supernatant, add in 2 mL phosphate buffer (pH 5.9) and 1 ml 0.04% tyrosine solution, keep the temperature at 37° C., incubated for 5 minutes, no red reaction is observed.

H. Amylase test: Inoculate the strain into BPA medium, with 0.2% soluble starch agar, culture for 2-5 days at 28° C. After obvious colonies are formed in agar plates, drop iodine solution (iodine 1.0 g KI 2.0 g, 300 mL distilled water) on the plate. Formation of transparent circle around colonies with no change of color indicates hydrolysis of starch.

The physiological and biochemical characteristics of the strain WSJ-IA is shown in Tab. 2.

2. The Analysis on Molecular Systematic Characteristics of WSJ-IA (1) 16S rDNA gene sequence:

16SrDNA is a part of the bacterial ribosome, it is the DNA sequence in the chromosome of a bacterium, which is responsible for encoding rRNA. Because it is highly conserved in genetics, its sequence has been generally recognized as one of the characteristics of bacterial molecular taxonomy.

Following 16SrDNA primers are used: 5'-AGAGTTTGATCMTGGCTCAG-3' (SEQ ID NO:11), 5'-GGTTACCTTGTTACGACTT-3' (SEQ ID NO:12).

Use the total DNA of bacterial strain WSJ-IA as template carry out PCR, the procedures are: 96° C. predenaturation for 1 min; in each of the 25 cycles, denature at 96° C. for 30 s, anneal at 50° C. for 30 s, extend at 72° C. for 1.5 min; subsequently, extend at 72° C. for 10 min to obtain the 1393 bp sequence (SEQ ID NO: 1), see Tab. 1.

TABLE 2

Physiological and biochemical characteristics of the strain WSJ-IA

| | Result |
|---|---|
| characteristics Utilization of carbon source | |
| glucose | + |
| mannose | + |
| mannitol | − |
| lactose | − |
| galactose | + |
| sorbose | − |
| sorbierite | − |
| maltose | + |
| saccharose | −− |
| melibiose | − |
| melezitose | − |
| rhamnose | − |
| raffinose | − |
| trehalose | + |
| fructose | − |
| xylose | − |
| ribose | − |
| synanthrin | − |
| salicine | + |
| amygdalin | − |
| euonymol | − |
| erythritol | − |
| myoinosito | − |
| glycerol | + |
| starch | + |
| glycogen | + |
| sodium gluconate | + |
| sodium malate | + |
| sodium succinate | + |
| sodium malonate | +w |
| Sodium tartarate | + |
| biochemical characteristics | |
| Liquefaction of gelatin | − |
| Milk reaction | peptonized |
| Reduction of nitrate | + |
| tyrosinase | − |
| Amylase | + |

Note
+: positive; −: negative; +w: weak positive

TABLE 3

Comparison of WSJ-IA 16S rDNA gene sequence with known bacteria

| Order number | Similar strain | homology % | NBRC serial number | NCBI serial number |
|---|---|---|---|---|
| 1 | Streptomyces flavidovirens | 99.353 | 13039(T) | AB184270 |
| 2 | Streptomyces albidochromogenes | 99.353 | 101003(T) | AB249953 |
| 3 | Streptomyces helvaticus | 99.281 | 13382(T) | AB184367 |
| 4 | Streptomyces chryseus | 99.281 | NRRL B-12347(T) | AY999787 |

Furthermore, this invention determined sequences of following five housekeeping genes commonly used in molecular taxonomy of *Streptomyces*, atpD gyrB, rpoB, recA and trpB in WSJ-IA strain. These are single-copied and protein encoding genes. They are structurally stable, there is no gap or stacking in these genes. Therefore, the sequencing results can be directly used to perform interspecific strain comparison on nucleotide—as well as the amino acid level, to further determine taxonomic status of WSJ-IA.

(2) Housekeeping Gene

A. atpD Gene Sequence atpD gene is a subunit of the ATP synthase. It is highly stable and common in microbial species, hence it is suitable to be a molecular marker for the germline categorization. In this invention following primers are used

```
                                    (SEQ ID NO: 13)
5'-GTCGGCGACTTCACCAAGGGCAAGGTGTTCAACACC-3'

(SEQ ID NO: 14)
5'-GTGAACTGCTTGGCGACGTGGGTGTTCTGGGACAGGAA-3'
```

Use the total DNA of bacterial strain WSJ-IA as template carry out PCR, the procedures are: 96° C. predenaturation for 1 min; in each of the 28 cycles, denature at 96° C. for 30 s, anneal at 63° C. for 30 s, extend at 72° C. for 1.0 min; subsequently, extend at 72° C. for 10 min to obtain the 680 bp sequence (SEQ ID NO: 2), see Tab. 2.

B. gyrB Gene Sequence gyrB is a subunit of DNA gyrase tetramer, it belongs to prokaryotes type II DNA topoisomerase. It regulates DNA topology by its effects of cutting and religating DNA, it has some relationship with the resistance of some antibiotic producing bacterium strains, and has high degree of stability and universality in microbial species, as a result it is suitable for molecular mark of phylogenetic classification. Therefore, its sequence has been generally recognized as one of the characteristics of bacterial molecular taxonomy.

Following primers are used in this invention:

Use the total DNA of bacterial strain WSJ-IA as template carry out PCR, the procedures are: 96° C. predenaturation for 1 min; in each of the 28 cycles, denature at 96° C. for 30 s, anneal at 65° C. for 30 s, extend at 72° C. for 1.5 min; subsequently, extend at 72° C. for 10 min to obtain the 1177 bp sequence (SEQ ID NO: 3), see Tab. 3.

C. rpoB Gene Sequence rpoB is a b-subunit of RNA polymerase, it is extensive present in *Streptomyces*.

Following primers are used in this invention:

```
                                    (SEQ ID NO: 15)
5'-GAGCGCATGACCACCCAGGACGTCGAGGC-3'

(SEQ ID NO: 16)
5'-CCTCGTAGTTGTGACCCTCCCACGGCATGA-3'
```

Use the total DNA of bacterial strain WSJ-IA as template, Carry out PCR, the procedures are: 96° C. predenaturation for 1 min; in each of the 28 cycles, denature at 96° C. for 30 s, anneal at 65° C. for 30 s, extend at 72° C. for 1.3 min; subsequently, extend at 72° C. for 10 min to obtain the 870 bp sequence (SEQ ID NO: 4), see Tab. 4.

D. RecA Gene Sequence

RecA is a recombinase, it plays an important role in the processes of DNA homologous recombination and repair of damaged DNA. The presence of RecA is a very important factor to ensure the stability of strain genomic DNA, therefore its sequence has been generally recognized as one of the characteristics of bacterial molecular taxonomy.

Following primers are used in this invention:

(SEQ ID NO: 17)
5'-CCGCRCTCGCACAGATTGAACGSCAATTC-3'

(SEQ ID NO: 18)
5'-GCSAGGTCGGGGTTGTCCTTSAGGAAGTTGCG-3'

Use the total DNA of bacterial strain WSJ-IA as template, carry out PCR, the procedures are: 96° C. predenaturation for 1 min; in each of the 28 cycles, denature at 96° C. for 30 s, anneal at 60° C. for 30 s, extend at 72° C. for 1.0 min; subsequently, extend at 72° C. for 10 min to obtain the 701 bp sequence (SEQ ID NO: 5), see Tab. 5.

E. TrpB Gene Sequence:

trpB gene encodes tryptophan synthase which is involved in the primary metabolism of *Streptomyces*, this gene is considered to have strain species specificity, its sequence has been generally recognized as one of the characteristics of bacterial molecular taxonomy.

Following primers are used in this invention:

(SEQ ID NO: 19)
5'-GCGCGAGGACCTGAACCACACCGGCTCACACAAGATCAACA-3'

(SEQ ID NO: 20)
5'-TCGATGGCCGGGATGATGCCCTCGGTGCGCGACAGCAGGC-3'

Use the total DNA of bacterial strain WSJ-IA as template, carry out PCR, the procedures are: 96° C. predenaturation for 1 min; in each of the 28 cycles, denature at 96° C. for 30 s, anneal at 66° C. for 30 s, extend at 72° C. for 1.0 min; subsequently, extend at 72° C. for 10 min to obtain the 611 bp sequence (SEQ ID NO: 6), see Tab. 6.

The results in Tabs. 3 and 4 show that there is no complete consistency between 16 SrDNA and five housekeeping gene sequences of the bacterial strain WSJ-IA, and gene sequences of known strains, so it can be decided that WSJ-IA might be a new species of *Streptomyces*.

was scooped to inoculate onto the seed medium (soybean cake flour 1.5%, starch 3.0%, NaCl 0.4%, $CaCO_3$ 0.5%, fish peptone 0.3%, $KH_2PO_4$ 0.05%), cultured at 28° C. for 48 hours in the stage A, subsequently transferred to stage B to culture at 28° C. for 24 hours, then transferred to 50 L seed tank, cultured for 36 hours, and subsequently transferred into a 2 ton fermentation tank to culture in seed medium (Culture medium: glucose 0.5%, starch 6.0%, yeast powder 0.5%, fishmeal 2.0%, $NH_4NO_3$ 0.6%, NaCl 1.0%, $CaCO_3$ 0.5%, $KH_2PO_4$ 0.05%, $MgSO_4$ 0.1%), fermentation was carried out at 28° C. to culture for 96 h. The supernatant of fermentation broth was sampled, diluted with pH 7.8~8.0 phosphate buffer containing 3% NaCl. *Bacillus* [CGMCC(B)63501] was used as test bacterium to determine the fermentation titer using the standard curve method in accordance with the Chinese Pharmacopoeia 2010 ed. II, Appendix XI in following medium: polypeptone 0.6%, beef extract powder 0.15%, yeast extract paste 0.6%, glucose 0.2%, agar 1.5-2.0%, with acetyl spiramycin as control. The experiment was repeated three times to obtain an average WSJ-IA fermentation titer of 1160 μg/ml, in comparison, fermentation with WSJ-2 strain containing ist single gene gave rise to an average titer of 280 μg/ml (Tab. 5).

Example 4

Yield Determination of the Product of Isovaleryl Spiramycin I Component Fermenting with WSJ-IA Strain The fermentation broth obtained in Example 3 was sampled, pH of the broth adjusted to 8.5, it was extracted with an equal volume of ethyl acetate, and the ethyl acetate extract concentrated to dryness, dissolved in methanol. The solution was separated using a Kromasil C18 column (4.5 mm×150 mm, 5 μm); mobile phase: methanol: sodium dihydrogen phosphate solution (53:47 v/v); detection wavelength: 231 nm; flow rate: 1.0 mL·$min^{-1}$; column temperature 25° C.; sample size: 10-20 μL. Contents of isovaleryl spiramycin I

TABLE 4

Comparisons of the housekeeping gene sequences of WSJ-IA with known bacteria

| | | | homology % | | Gene bank serial number | |
| --- | --- | --- | --- | --- | --- | --- |
| | Similar strains | | | Amino | | Amino |
| gene | nucleotides | Amino acids | nucleotides | acids | nucleotides | acids |
| atpD | S. griseus subsp. griseus NBRC13350 | S. griseus subsp. griseus NBRC13350 | 96 | 99 | AP009493 | YP0018236 75C13350 |
| gyrB | S. spiroverticillatus | S. spiroverticillatus | 93 | 94 | AB014337 | AB072882 |
| rpoB | S. avermitilis MA-4680 | S. avermitilis MA-4680 | 94 | 93 | BA000030 | NP_826091 |
| recA | S. avermitilis MA-4680 | S. avermitilis MA-4680 | 91 | 95 | BA000030 | NP_823668 |
| trpB | S. griseus subsp. griseus NBRC13350 | S. flavogriseus ATCC 33331 | 92 | 99 | AP009493 | ZP_05806307 |

Note:
S: *Streptomyces*

Example 3

Determination of Pilot-scale Fermentation Titer of WSJ-IA Bacteria Strain

WSJ-IA strain was cultured in the slant medium described in Example 2 at 28° C. for 7-10 days, a piece of above culture component in the broth was calculated using the HPLC results (FIG. 3). The results from 3 experiments showed that, fermenting with WSJ-IA strain and WSJ-2 strain containing ist monogene, the average total content of isovaleryl spiramycin I component was 12.061% and 7.088%, respectively. After fermentation in accordance with Example 3, the fermentation titers of the two strains were measured with microbiological assay, and the products were analyzed using HPLC (FIG. 3). According to the HPLC peak areas obtained, isovaleryl spiramycin I component produced with the two strains were compared, the ratio of isovaleryl spiramycin I vs. spiramycin produced with the two strains, respectively, calculated. The results showed that introduction of ist-acyB2 gene increased the fermentation titer of the WSJ-IA by 414%, the produced isovaleryl spiramycin I content was increased by 170.2%, meanwhile, the production of spiramycin was decreased accordingly. This increased the ratio between isovaleryl spiramycin I content and spiramycin content by 218% (Tab. 5).

This invention provides a strain capable of producing isovaleryl spiramycin I containing ist-acyB2 gene, under a certain fermentation condition, This strain increases the production of isovaleryl spiramycin I by a factor of 1.7, and increases the fermentation titer by a factor of 4.14 in comparison with the strain containing only ist gene.

TABLE 5

Comparison of the fermentation titer using WSJ-IA and WSJ-2 strains and component contents

| Strains | fermentation titer (μg/mL) | Spiramycin peak area (%) | Isovaleryl spiramycin I peak area(%) | Isovaleryl spiramycin I/ spiramycin(%) |
|---|---|---|---|---|
| WSJ-2 | 1. 260 | 1. 61.146 | 1. 6.980 | 1. 11.42 |
| | 2. 280 | 2. 63.756 | 2. 7.150 | 2. 11.21 |
| | 3. 300 | 3. 62.223 | 3. 7.134 | 3. 11.47 |
| | average 280 | average 62.375 | average 7.088 | average 11.36 |
| WSJ-IA | 1. 1040 | 1. 47.825 | 1. 10.956 | 1. 22.91 |
| | 2. 1250 | 2. 48.982 | 2. 13.013 | 2. 26.57 |
| | 3. 1190 | 3. 49.527 | 3. 12.214 | 3. 24.66 |
| | average 1160 | average 48.778 | average 12.061 | average 24.72 |

The invention claimed is:

1. A genetically engineered *Streptomyces* strain designated as WSJ-IA and deposited under the accession number CGMCC 3942.

2. A method for producing isovaleryl spiramycin I, the method comprising recovering the isovaleryl spiramycin I from a fermentation broth produced by culturing the genetically engineered *Streptomyces* strain according to claim 1 in a culture medium.

* * * * *

SEQUENCE LISTING

<160> NUMBER OF SEQ ID NOS: 20

<210> SEQ ID NO 1
<211> LENGTH: 1393
<212> TYPE: DNA
<213> ORGANISM: Streptomyces spiramyceticus

<400> SEQUENCE: 1

```
ccttcgacag ctccctccca caaggggttg ggccaccggc ttcgggtgtt accgactttc      60
gtgacgtgac gggcggtgtg tacaaggccc gggaacgtat tcaccgcagc aatgctgatc     120
tgcgattact agcaactccg acttcatggg gtcgagttgc agaccccaat ccgaactgag     180
accggctttt tgagattcgc tccgcctcgc ggcatcgcag ctcattgtac ggccattgta     240
gcacgtgtgc agcccaagac ataaggggca tgatgacttg acgtcgtccc caccttcctc     300
cgagttgacc ccggcggtct cctgtgagtc cccatcaccc cgaagggcat gctggcaaca     360
caggacaagg gttgcgctcg ttgcgggact taacccaaca tctcacgaca cgagctgacg     420
acagccatgc accacctgta taccgaccac aaggggggcac ctatctctag gtgtttccgg     480
tatatgtcaa gccttggtaa ggttcttcgc gttgcgtcga attaagccac atgctccgct     540
gcttgtgcgg gcccccgtca attcctttga gttttagcct tgcggccgta ctccccaggc     600
ggggaactta atgcgttagc tgcggcaccg acgacgtgga atgtcgccaa cacctagttc     660
ccaacgttta cggcgtggac taccagggta tctaatcctg ttcgctcccc acgctttcgc     720
tcctcagcgt cagtaatggc ccagagatcc gccttcgcca ccggtgttcc tcctgatatc     780
tgcgcatttc accgctacac caggaattcc gatctccct accacactct agcctgcccg     840
tatcgaatgc agacccgggg ttaagcccg  ggctttcaca tccgacgcga caagccgcct     900
acgagctctt tacgcccaat aattccggac aacgcttgcg ccctacgtat taccgcggct     960
gctggcacgt agttagccgg cgcttcttct gcaggtaccg tcactttcgc ttcttccctg    1020
ctgaaagagg tttacaaccc gaaggccgtc atccctcacg cggcgtcgct gcatcaggct    1080
ttcgcccatt gtgcaatatt ccccactgct gcctcccgta ggagtctggg ccgtgtctca    1140
gtcccagtgt ggccggtcgc cctctcaggc cggctacccg tcgtcgcctt ggtaggccat    1200 tacccacca acaagctgat aggccgcggg ctcatccttc accgccggag cttttaaccc     1260
ccacccatgc aggcaggagt gttatccggt attagaccc gtttccaggg cttgtcccag    1320
agtgaagggc agattgccca cgtgttactc acccgttcgc cactaatcca ccccgaaggg    1380
```
cttcatcgtt cga                                                         1393

<210> SEQ ID NO 2
<211> LENGTH: 680
<212> TYPE: DNA
<213> ORGANISM: Streptomyces spiramyceticus

<400> SEQUENCE: 2
agcttgtcct cttcgcccag ctcgtcgata ccgaggatcg cgatgatgtc ctggaggtcc      60
ttgtacttct gcaggattcc cttgacgcgg ctggccgcgt cgtagtggtc ctgcgtgatg     120
tagcgggggt ccaggatgcg ggacgtcgag tccagcgggt cgaccgccgg gtagatgccc     180
ttctccgaga tcgggcgcga cagaacggtc gtcgcgtcca ggtgggcgaa ggtggtcgcc     240
ggcgccgggt cggtcaggtc gtccgcgggg acgtagatcg cctgcatcga ggtgatcgag     300
tgaccacgcg tcgaggtgat gcgctcctgg agcacaccca tctcgtcggc cagggtcggc     360
tggtaaccca ctgcggacgg catacggccg agcagcgtgg agacctcgga accggcctgg     420
gtgaagcgga agatgttgtc gatgaagagc agcacgtcct gcttctgaac atcgcggaag     480
tactccgcca tggtcagggc ggacagggcg acgcgcagac gcgtgcccgg cggctcgtcc     540
atctggccga agaccagcgc ggtcttgtcc agaaacacccg attcggtcat ctcgtcgatg     600
aggtcgttgc cctcacgggt gcgctcgccg acaccggcga acaccgacac accctcgtgc     660
agcttcgcca cacgcatgat                                                  680

<210> SEQ ID NO 3
<211> LENGTH: 1177
<212> TYPE: DNA
<213> ORGANISM: Streptomyces spiramyceticus

<400> SEQUENCE: 3
ccggcggtct gcacggcgtc ggcgtctccg tggtgaacgc gctgtcgtcg aaggtcgctg      60
tcgaggtcaa gcgcgacggt taccgctgga cgcaggacta caagctcggt gtgccgacgg     120
cgccgctggc ccgtaacgag gccacggagg agtccggtac ctctgtcacc ttctgggccg     180
acccggacgt cttcgagacg accgactact ccttcgagac gctgtcgcgg cgtttccagg     240
agatggcgtt cctcaacaag ggcctgacgc tcaagctgac ggacgagcgg gagtccgcga     300
aggccgtggc gggggcggac acggcggacg gtacggagga cgaccaggtc cgtacggtca     360
cgtaccacta cgaaggcggc atcgtcgact tcgtgaagta cctgaactcg cgcaagggtg     420
agctgattca cccgaccgtc atcgacgtcg aggccgagga caaggagcgc atgctctcgg     480
tcgagatcgc gatgcagtgg aactcgcagt acaccgaggg tgtctactcc ttcgcgaaca     540
cgatccacac gcacgagggc ggcacgcacg aagagggctt ccgtgcggcg atgacaggtc     600
tggtcaaccg gtacgcgcgc gagaagaagt tcctgcgtga aaggacgac aacctcgccg     660
gtgaggacat ccgtgagggt ctgacggcga tcatctcgat caagctgggc gagccgcagt     720
tcgagggtca gacgaagacc aagctgggca acacggaggc gaagaccttc gtgcagaagg     780
tcgtgcacga gcacctcaac gactggttcg accgcaatcc gaacgaggcc gcggacatca     840
tccgcaagtc gatccaggcg gccacggcgc gtcgcggc ccgcaaggcg cgcgacctga     900
cccgtcgcaa gggcctgctg gagtcggcct cgctgccggg caagctgtcc gactgccagt     960
cgaacgaccc gacgaagtgc gagatcttca tcgtcgaggg tgactccgcc ggtggctcgg    1020
cgaagtccgg tcgtaacccg atgtaccagg ccatcctgcc gatccgaggc aagatcctga    1080
acgtcgagaa ggcgcggatc gacaagatcc tccagaacac cgaggtccag gcgctgatct    1140
cggcgttcgg cacgggtgtg cacgaggact tcgacat                            1177

<210> SEQ ID NO 4
<211> LENGTH: 870
<212> TYPE: DNA
<213> ORGANISM: Streptomyces spiramyceticus

<400> SEQUENCE: 4
gtcgtcgcct ccatcaagga gttcttcggc accacccagc tgtcgcagtt catggaccag     60
aacaacccgc tgtcgggtct cacccacaag cgccgtctgt cggcgcttgg cccgggtggt    120
ctctcccgtg agcgggccgg cttcgaggtc cgtgacgtgc accgtctca ctacggccgc     180 atgtgcccga ttgagacccc tgaaggcccg aacatcggtc tgatcggttc gctcgcctcg    240 tacgccgcg tcaacgcgtt cggcttcgtc gagacgccgt accgcaaggt cgtcgacggt     300
gtcgtcaccg acgacgtcga ctacctgacg gccgacgaag aggaccgctt cgtcatcgcg    360
caggccaacg cgacgctctc cgaggacatg cgcttcgagg agtcccgcgt cctggtccgc    420
cgtcgtggcg gcgagatcga ctacatcccg ggcgacgacg tcgactacat ggacgtctcg    480
ccgcgccaga tggtgtcggt cgcgaccgcg atgatcccgt tcctcgagca cgacgacgca    540
aaccgcgcgc tcatgggcgc gaacatgatg cgtcaggccg tgccgctgat cacgtccgag    600
gcgccgctcg tcggcaccgg catggaatac cgctgtgcgg tcgacgccgg tgacgtcatc    660
aaggcggaga aggagggcgt ggtccaggag gtttccgcgg actacgtcac cgtcgccaac    720
gacgacggta cgtacaccac gtaccgcatc gccaagttct cccgctccaa ccagggcacc    780
tcggtcaacc agaaggttgt cgtcgacgag ggtgcccggg tcgtcgaggg ccaggtcctc    840
gccgacgggc cgccacccca gcagggtgag                                    870

<210> SEQ ID NO 5
<211> LENGTH: 701
<212> TYPE: DNA
<213> ORGANISM: Streptomyces spiramyceticus

<400> SEQUENCE: 5
accggccgac gacccccatcg aggtcatctc caccgggtcg accgctctgg acatcgcgct     60
cggcgtcggc ggactgccgc gcggtcgtgt ggtggaggtg tacggaccgg aatcctccgg    120
taagacgaca ctgacgctgc acgccgtggc caacgcgcag aaggccggtg caccgtcgc     180 cttcgtggat gccgagcacg cgctcgaccc cgaatacgcc aaggcactcg gcgtcgacac    240
ggacaatctg atcctctccc agccggacac cggcgagcag ccctcgaga tcgtggacat     300 gctggtccgc tcgggcgcca tcgacctcat cgtcattgac tccgtcgccg ccctggtgcc    360
gcgcgcggag attgagggtg agatgggcga ctcgcacgtc ggcctccagg cccggctgat    420
gagccaggcg ctgcgcaaga tcactggcgc gctgcaccag tcccagacca cagcgatctt    480
catcaaccag ctccgcgaga agatcggtgt gatgttcggc tccccggaga ccacgacagg    540
tggccgggcg ctgaagttct acgcctccgt gcggctcgac atccgccgta tcgagaccct    600
caaggacggc acggacgcgg tcggcaaccg caccccgcgt caaggtcgtca aaaacaaggt    660 cgcgccgccg ttcaagcagg ccgagttcga catcctctac g                       701

<210> SEQ ID NO 6
<211> LENGTH: 611
<212> TYPE: DNA
<213> ORGANISM: Streptomyces spiramyceticus -continued

```
<400> SEQUENCE: 6
gctcaccaag cgcatgggca agacgcgcgt gatcgcggag accggcgccg gccagcacgg      60
cgtcgccacc gccaccgcgt gcgccctctt cggcctcgaa tgcaccatct acatgggcga    120
gatcgacacc gagcgccagg cgctcaacgt cgcccgcatg cggatgctcg gtgccgaggt    180
cgtcgccgtg aagtccggca gccgcaccct gaaggacgcc atcaacgagg cgttccgcga    240
ctgggtcgcc aatgtcgacc gtacgcacta cctcttcggc acggtcgccg gcccgcaccc    300
cttccccgcc atggtccgcg acttccaccg ggtcatcggt gtcgaggcac gccgccagat    360
cctggagcgc acgggacggc tgcccgacgc ggcggtcgcc tgcgtcggcg gcgggtccaa    420
cgccatcggt ctcttccacg ccttcatccc ggacgcggac gtacgtctca tcggctgcga    480
gcccgccggg cacggcatcg agaccggcga gcacgcggcc accctgtccg cgggcgagcc    540
cggcatcctg cacggctcgc ggtcgtacgt cctccaggac gaggagggcc agatcaccga    600
gccctactcg a                                                         611

<210> SEQ ID NO 7
<211> LENGTH: 19
<212> TYPE: DNA
<213> ORGANISM: artificial sequence
<220> FEATURE:
<223> OTHER INFORMATION: p1

<400> SEQUENCE: 7 cgctc aggga cgcaa gacc                                                19

<210> SEQ ID NO 8
<211> LENGTH: 28
<212> TYPE: DNA
<213> ORGANISM: artificial sequence
<220> FEATURE:
<223> OTHER INFORMATION: p2

<400> SEQUENCE: 8 ccgga attcg ccccg tgacc tcacc gtc                                     28

<210> SEQ ID NO 9
<211> LENGTH: 18
<212> TYPE: DNA
<213> ORGANISM: artificial sequence
<220> FEATURE:
<223> OTHER INFORMATION: p3

<400> SEQUENCE: 9 gaggt agaag gcgaa ggt                                                 18

<210> SEQ ID NO 10
<211> LENGTH: 18
<212> TYPE: DNA
<213> ORGANISM: artificial sequence
<220> FEATURE:
<223> OTHER INFORMATION: p4

<400> SEQUENCE: 10 cgtca gatgc cagtt cac                                                 18

<210> SEQ ID NO 11
<211> LENGTH: 20
<212> TYPE: DNA
<213> ORGANISM: artificial sequence
<220> FEATURE:
<223> OTHER INFORMATION: 16SrDNA primer
```

-continued

<400> SEQUENCE: 11 agagt ttgat cmtgg ctcag                                         20

<210> SEQ ID NO 12
<211> LENGTH: 19
<212> TYPE: DNA
<213> ORGANISM: artificial sequence
<220> FEATURE:
<223> OTHER INFORMATION: 16SrDNA primer

<400> SEQUENCE: 12 ggtta ccttg ttacg actt                                          19

<210> SEQ ID NO 13
<211> LENGTH: 36
<212> TYPE: DNA
<213> ORGANISM: artificial sequence
<220> FEATURE:
<223> OTHER INFORMATION: atpD primer

<400> SEQUENCE: 13 gtcgg cgact tcacc aaggg caagg tgttc aacac c                     36

<210> SEQ ID NO 14
<211> LENGTH: 38
<212> TYPE: DNA
<213> ORGANISM: artificial sequence
<220> FEATURE:
<223> OTHER INFORMATION: atpD primer

<400> SEQUENCE: 14 gtgaa ctgct tggcg acgtg ggtgt tctgg acagg aa                    38

<210> SEQ ID NO 15
<211> LENGTH: 29
<212> TYPE: DNA
<213> ORGANISM: artificial sequence
<220> FEATURE:
<223> OTHER INFORMATION: rpoB primer

<400> SEQUENCE: 15 gagcg catga ccacc cagga cgtcg aggc                              29

<210> SEQ ID NO 16
<211> LENGTH: 30
<212> TYPE: DNA
<213> ORGANISM: artificial sequence
<220> FEATURE:
<223> OTHER INFORMATION: rpoB primer

<400> SEQUENCE: 16 cctcg tagtt gtgac cctcc cacgg catga                             30

<210> SEQ ID NO 17
<211> LENGTH: 29
<212> TYPE: DNA
<213> ORGANISM: artificial sequence
<220> FEATURE:
<223> OTHER INFORMATION: RecA primer

<400> SEQUENCE: 17 ccgcr ctcgc acaga ttgaa cgsca attc                              29

<210> SEQ ID NO 18

```
<211> LENGTH: 32
<212> TYPE: DNA
<213> ORGANISM: artificial sequence
<220> FEATURE:
<223> OTHER INFORMATION: RecA primer

<400> SEQUENCE: 18 gcsag gtcgg ggttg tcctt sagga agttg cg                                32

<210> SEQ ID NO 19
<211> LENGTH: 41
<212> TYPE: DNA
<213> ORGANISM: artificial sequence
<220> FEATURE:
<223> OTHER INFORMATION: trpB primer

<400> SEQUENCE: 19 gcgcg aggac ctgaa ccaca ccggc tcaca caaga tcaac a                      41

<210> SEQ ID NO 20
<211> LENGTH: 40
<212> TYPE: DNA
<213> ORGANISM: artificial sequence
<220> FEATURE:
<223> OTHER INFORMATION: trpB primer

<400> SEQUENCE: 20 tcgat ggccg ggatg atgcc ctcgg tgcgc gacag caggc                        40
```